(12) United States Patent
Rayton et al.

(10) Patent No.: US 7,595,171 B2
(45) Date of Patent: Sep. 29, 2009

(54) **KETOCAROTENOIDS FROM *ADONIS PALAESTINA***

(75) Inventors: Simon Rayton, Hong Kong (CN); John Rayton, Hong Kong (CN); Linda Foley, Killorglin (IE); Peter Wyn Jones, Cork (IE)

(73) Assignee: Sinotrade Technology Limited, Hong Kong (CN)

( * ) Notice: Subject to any disclaimer, the term of this patent is extended or adjusted under 35 U.S.C. 154(b) by 2 days.

(21) Appl. No.: 11/381,288

(22) Filed: May 2, 2006

(65) Prior Publication Data

US 2006/0260010 A1 Nov. 16, 2006

Related U.S. Application Data

(60) Provisional application No. 60/677,664, filed on May 3, 2005.

(51) Int. Cl.
*C12P 23/00* (2006.01)

(52) U.S. Cl. .................. 435/67; 424/725; 424/778; 800/260; 800/323

(58) Field of Classification Search .................. 435/67; 424/725, 778; 800/260, 323
See application file for complete search history.

(56) References Cited

U.S. PATENT DOCUMENTS

| 2,918,370 | A | | 12/1959 | Helgren |
| 4,670,247 | A | | 6/1987 | Scialpi |
| 5,043,170 | A | | 8/1991 | Borenstein et al. |
| 5,258,189 | A | | 11/1993 | Efstathiou |
| 5,382,714 | A | | 1/1995 | Khachik |
| 5,453,565 | A | * | 9/1995 | Mawson ...................... 435/67 |
| 5,605,699 | A | | 2/1997 | Bernhard et al. |
| 5,648,564 | A | | 7/1997 | Ausich et al. |
| 5,695,794 | A | | 12/1997 | Stark et al. |
| 5,849,345 | A | | 12/1998 | Giger et al. |
| 5,935,624 | A | | 8/1999 | DeLuca et al. |
| 6,433,025 | B1 | | 8/2002 | Lorenz |
| 7,329,789 | B1 | * | 2/2008 | Schonemann et al. ....... 585/351 |

OTHER PUBLICATIONS

Internet website http://www.seedman.com—web archived on Jan. 2004; (retrieved on Mar. 6, 2008) (17 pages total).*
Internet website: http://www.ncbi.nlm.nih.gov/Taxonomy/Browser/wwwtax.*
Tcyczkowski et al., *Poultry Sci.*, 70(3):651-654, 1991.
Kamata et al., *Comp. Biochem. Physiol.*, 86B(3):587-591, 1987.
Yuan et al., *J. Agric. Food Chem.*, 47:31-35, 1999.
Lorenz, *BioAstin/NatuRose Technical Bulletin* #020, 2001.
Lorenz, *NatuRose Technical Bulletin* #078, 2000.
Lorenz, *BioAstin Technical Bulletin* #062, 2000.
Lorenz, *NatuRose Technical Bulletin* #060, 1999.
Tanaka et al., *Carcinogenesis*, 15(1):15-19 (1994).
Jyonouchi et al., *Nutrition and Cancer*, 19(3):269-280 (1993).
Jyonouchi et al., *Nutrition and Cancer*, 16(2):93-105 (1991).
Misawa et al., *J. Bacteriol.*, 177:6575-6584 (1995).

* cited by examiner

*Primary Examiner*—Susan B McCormick Ewoldt
(74) *Attorney, Agent, or Firm*—Husch Blackwell Sanders Welsh & Katz LLP

(57) ABSTRACT

Methods for the production of new *Adonis palaestina* plants and plant populations with improved characteristics such as increased flower size, astaxanthin content, and/or reduced cardenolide content are provided. Also provided are an astaxanthin-containing *Adonis* oleoresin and methods of extracting astaxanthin and other ketocarotenoids from flowers of *Adonis palaestina* plants, while reducing non-ketocarotenoids and cardenolides.

7 Claims, No Drawings

KETOCAROTENOIDS FROM *ADONIS PALAESTINA*

CROSS-REFERENCE TO RELATED APPLICATION

This application is based on Ser. No. 60/677,664 filed on May 3, 2005, whose disclosures are incorporated by reference.

TECHNICAL FIELD

The present invention relates to the production and characteristics of new *Adonis palaestina* plants and plant populations with improved characteristics such as increased flower size, improved astaxanthin content in flowers and/or reduced cardenolide content. The invention further relates to a method of extracting astaxanthin and other ketocarotenoids from *Adonis palaestina* flowers, while reducing non-ketocarotenoids and cardenolides in the resulting extract.

BACKGROUND

Carotenoid pigments can be grouped into one or the other of two $C_{40}$ families: the hydrocarbon carotenes or the oxygenated xanthophylls. The xanthophylls that are derivatives of β-carotene typically contain a hydroxyl or keto group or both in one or both of the β-ionene rings present in the xanthophyll molecule, thereby providing a number of possible structurally similar compounds. Xanthophylls containing only hydroxyl groups tend to be yellow pigments, whereas those containing at least one keto group tend to be redder pigments.

Astaxanthin [3,3'-dihydroxy-β,β-carotene-4,4'-dione; structural formula below] is a xanthophyll carotenoid that occurs particularly in a wide variety of marine animals including red fishes such as sea bream and salmon, and crustaceans such as crab, lobster, and shrimp.

Misawa et al., *J. Bacteriol.*, 177:6575-6584 (1995). From studies of the properties of astaxanthin, it is a carotenoid of great interest to the pharmaceutical, "nutraceutical" (as a pre-cursor to vitamin A and other properties), and food industries. The complete biomedical properties of astaxanthin remain to be elucidated, but initial results suggest that it could play an important role in cancer and tumor prevention, as well as eliciting a positive response from the immune system and as an anti-inflammatory agent. See Tanaka et al., *Carcinogenesis*, 15(1):15-19 (1994); Jyonouchi et al., *Nutrition and Cancer*, 19(3):269-280 (1993); and Jyonouchi et al., *Nutrition and Cancer*, 16(2):93-105 (1991).

U.S. Pat. No. 6,433,025 to Lorenz teaches that astaxanthin can be used to retard or prevent sunburn when administered at an amount of about 1 to about 100 milligrams (mg) per day, and preferably about 2 to about 10 mg per day. The astaxanthin can be administered in a composition by a peroral, topical or injectable route.

Sources of astaxanthin include crustaceans such as a krill in the Antarctic Ocean, cultured products of the yeast *Phaffia rhodozyma*, cultured products of a green alga *Haematococcus pluvialis*, and products obtained by organic synthetic methods. However, when crustaceans such as krill or the like are used, a great deal of work and expense are required for the isolation of astaxanthin from contaminants such as lipids and the like during the harvesting and extraction. Moreover, in the case of the cultured product of the yeast *Phaffia*, a great deal of expense is required for the gathering and extraction of astaxanthin because the yeast has rigid cell walls and produces astaxanthin only in a low yield.

*H. pluvialis* produces one of the highest levels of astaxanthin (0.5-2 percent dry weight) among organisms, with the astaxanthin synthesized by this alga being present mostly as the mono-long chain ester (70% of the carotenoid fraction), along with a smaller amount of di-long chain ester (10% of the carotenoid fraction). Free astaxanthin (5% of the carotenoid fraction) is also present as are β-carotene, canthaxan-

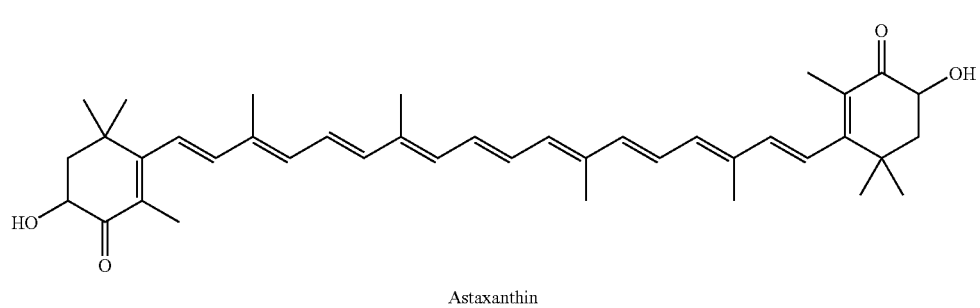

Astaxanthin

Because animals generally cannot biosynthesize carotenoids, they obtain those carotenoids present in microorganisms or plants upon which they feed. For this reason, astaxanthin has been widely used as a feed additive in aquaculture for the purpose of red color enhancement in the production of cultured fish and shellfish such as sea bream, salmon, and shrimp and the like. Astaxanthin also has uses in providing pigment to poultry (broiler skin and egg yolks), avian plumage, and ornamental fish such as Koi.

Astaxanthin has also been found to have diverse biological functions. It is a vitamin A precursor, acts as a scavenger and/or quencher of free radicals and active oxygen species, and has been shown to enhance the immune response. See thin and lutein. See, BioAstin/NatuRose™ Technical Bulletin #015, Cyanotech Corporation (2001). Extraction from *H. pluvialis* is difficult because of cell wall properties of this alga. Furthermore, *H. pluvialis* needs high light levels for astaxanthin formation and has to be cultured under special conditions.

For these reasons, astaxanthin produced from biological sources is often deemed to be inferior to that obtained by the organic synthetic methods on the basis of cost. The organic synthetic methods however have a problem of by-products produced during the synthesis because of use of astaxanthin as a feed for fish and shellfish, and as an additive to foods. The products obtained by the organic synthetic methods can be contrary to some consumer's preference for naturally produced products.

Thus, there is a need for a natural and economic source of astaxanthin that consumers regard as desirable. It would be desirable to supply an inexpensive astaxanthin that is free from contaminating side products and is produced from a biological source.

Astaxanthin and other ketocarotenoids also occur in certain plants, especially certain species belonging to the family Ranunculaceae and genus *Adonis*. *Adonis vernalis*, *Adonis aestivalis* and *Adonis palaestina* are species of the genus *Adonis* that produce astaxanthin in their flower petals.

Species of the genus *Adonis* also produce mixtures of cardenolides in their flowers. Because the cardenolides are produced in the flowers, the flowers cannot be fed without pre-treatment to fish or other animals because the cardenolides are toxic to fish and to other animals at high concentrations. Therefore, there is a need to reduce or eliminate cardenolides from astaxanthin preparations derived from *Adonis*.

*Adonis* is the common name for dried plant material, extracts and tinctures containing astaxanthin and cardenolides from the yellow-flowered perennial species *Adonis vernalis*. The cardenolides are used in herbal medicine ("phytomedicine") and homoeopathy for the treatment of heart arrhythmia and kidney disease. Cardenolides act very much like digitalis (from foxglove; widely used in conventional as well as alternative medicine). *Adonis* preparations have the advantages of acting more rapidly than digitalis and are non-cumulative.

Germany and France are the principal consumers of *Adonis* in herbal medicine, whereas Bulgaria, Hungary, Russia, Romania and the Ukraine are the major suppliers. The vast majority of *A. vernalis* harvested is collected from the wild, rather than being cultivated, particularly in Russia, Romania and the Ukraine.

By 1998, unsustainable harvesting in Russia had reduced *A. vernalis* stocks to dangerously low levels. *A vernalis* is now included in the Red Data books (listing endangered species) of most of the countries comprising its range, and harvesting from the wild is prohibited by law in a number of countries.

Domesticating species of the genus *Adonis* or trying to achieve large-scale cultivation of *A. vernalis* is very difficult because of problems obtaining either self- or cross-pollinated seed, problems associated with poor germination (including almost complete loss of seed viability following storage for 12 months), delay in reaching harvestable flower size (up to 4 years from sowing), and low yields. Another problem with many *Adonis* species is that they have to be harvested by hand to insure the collection of flowers and not other parts of the plant. Plants currently cannot be grown in large numbers or the flowers harvested mechanically.

U.S. Pat. No. 5,453,565 to Mawson discloses a new strain of *Adonis aestivalis* that is said to have an average of 18-22 petals per flower head and contain an average of 200-350 µg of astaxanthin pigment per flower head. Methods of extracting astaxanthin are also disclosed. Seeds of that strain were said to be deposited on 18 Jul. 1990 with the National Collection of Industrial and Marine Bacteria Limited, Aberdeen under Accession No. NCIMB 40309, in accordance with the Budapest Treaty. The plants that mature from that deposited strain are referred to under the denomination *Adonis aestivalis* L. 'Loders Red'. Those plants are also subject to Plant Breeders Rights that can be found at file number 19981166 of Aug. 28, 1998, grant number 6243 dated Jun. 5, 2000, that expires on Dec. 31, 2025.

Flowers of the species *Adonis palaestina* produce astaxanthin, other hydroxycarotenoids and hydroxyketocarotenoids primarily in the petals of the bright red flowers as di-long chain fatty acid esters. This species of the genus *Adonis* has heretofore not been rigorously examined as a commercial source of astaxanthin. The present inventors have now examined this species and found it to be readily improvable to provide for the commercial production of astaxanthin diesters and mixtures of those diesters with other carotenoids. The description that follows describes several of these improved plants.

BRIEF SUMMARY OF THE INVENTION

The present invention relates to improved *Adonis palaestina* plants whose flowers provide enhanced amounts of astaxanthins well as a method of producing astaxanthin and other ketocarotenoids from those *Adonis palaestina* plants.

Illustrative, standard *Adonis palaestina* flowers have a diameter of about 1.9 cm, a diameter of the so-called eye in the petals surrounding the stamens and pistils that contains anthocyanin pigments, and contain an average of 8-12 petals per flower head. Those flowers contain an average of about 0.21 milligrams of astaxanthin per gram of flower and about 7.9 g of astaxanthin per kg of dried petals. The dried petals contain about 10 to about 15% water. On the other hand, flowers of the contemplated plants of this invention have a mean flower diameter of about 4 cm to about 8 cm, a mean eye diameter of about 1.4 cm, a mean number of petals per flower head of about 8, and a mean astaxanthin content of at least about 0.4 mg/flower (dried) or about 17.6 g/kg of dried petals. The extracted carotenoids of a contemplated flower contain about 75 to about 90 weight percent astaxanthin mono-ester, di-ester and free astaxanthin, along with about 5 to about 10 weight percent lutein, about 2.5 to about 5 weight percent adonixanthin and less than about 1 percent of adonirubin, β-carotene, 3-hydroxyechinenone and 4-hydroxyechinenone.

Thus, it has been found that the astaxanthin concentration in flowers (g/kg plant tissue dry weight) can be increased as can the astaxanthin yield (kg/ha); whereas the cost of extraction can be reduced as can the content of non-ketocarotenoids and of cardenolides in the oleoresin. Improvements in the extraction techniques and process can also help lower the cost of extraction and reduce the content of cardenolides.

The plants from which astaxanthin is extracted represent improved strains of *Adonis palaestina*. The present invention also provides for methods of selecting and further improving the genetic backgrounds, varieties and populations of *Adonis palaestina*.

In another embodiment, the extraction method uses a petal-only preparation and results in producing an oleoresin that has 95% of the oleoresin carotenoids present as astaxanthin and other ketocarotenoids. In another embodiment of the present invention, the astaxanthin content of the flower head dry weight is about 35 g per kg dry flower weight, representing a higher proportion of astaxanthin in the total carotenoid content, whereas the cardenolide content is reduced.

The pigment quantities are determined by high performance liquid chromatography (HPLC) of a dried flower petal or leaf extract so that the amount of each of astaxanthin (or other pigment) is measured in the di-esterified form that is often present in the fresh flower petal and provided as a calculated amount of the free astaxanthin (a diketodiol). Pigment quantities can also be determined as grams (g) of astaxanthin per kilogram (kg) of plant tissue dry weight measured using the absorbance of a hexane solution measured at 467 nm and an extinction coefficient of 2100 as is shown hereinafter.

An oleoresin comprised of free or a mixture of $C_8$-$C_{20}$ fatty acid mono- or di-esters of astaxanthin is also contemplated; i.e., the fatty acid chains are of a plurality of chain lengths and/or levels of ethylenic unsaturation. A contemplated oleoresin is an extract that contains a high level of the free xanthophyll and xanthophyll fatty acid esters and is about 99 percent and preferably about 99.9 percent free of the extracting organic solvent; i.e., contains less than about 1 percent and preferably less than about 0.1 percent organic solvent by weight. The resulting solvent-free extract is referred to as an *Adonis* oleoresin or more preferably as an astaxanthin-containing *Adonis* oleoresin.

A composition suitable for use as a food or feed supplement or use in nutraceutical, cosmaceutical, and pharmaceutical applications is also an embodiment of the present invention. Such a composition comprises a purified astaxanthin-containing concentrate prepared from an astaxanthin-containing *Adonis* oleoresin that is dissolved or dispersed in a diluent. A contemplated diluent can be a solid such as a wax or hydrocarbon that is solid at about 40° C., a liquid or a gel at ambient temperatures. One embodiment of a purified concentrate is a solid to semi-solid that includes the mixed esters of astaxanthin of an *Adonis* oleoresin present at about 2 to about 10 percent by weight, and preferably at about 5 percent by weight. In some preferred embodiments, the concentrate includes at least one additional carotenoid in free or esterified form in a different concentration from that found in *Adonis* oleoresin. Thus, some embodiments contain a carotenoid not present in the oleoresin, whereas other embodiments contain a carotenoid present in the oleoresin, but in an amount that is enhanced by at least 10 percent and preferably by at least 20 percent over that present in the oleoresin. The added carotenoid can be present in an amount that is several times that found in the oleoresin.

A composition suitable for use as a food supplement for human or other animals such as poultry like chickens and turkeys, fish like trout, sea bream and salmon, as well as crustaceans like shrimp, lobsters and crabs is also contemplated. A contemplated food supplement can be used to provide color to the meat or skin of those animals as well as to the eggs of such animals, and particularly chickens.

The food supplement comprises an astaxanthin-containing *Adonis* oleoresin having a reduced cardenolide content as discussed before that is dissolved or dispersed in a comestible medium. This food supplement can thus be prepared by suitable purification of a before-described oleoresin as by extraction, dissolution, filtration and removal of cardenolides, followed by dissolution or dispersion of the purified carotenoids in an appropriate comestible medium such as an edible vegetable oil.

One use of the diluted purified carotenoid composition aspect of the invention is a nutritionally effective amount of the astaxanthin in a unit dosage form suitable for oral administration such as packets, tablets, capsules, and powders in vials or ampoules. Another use of this aspect of the invention includes a nutritionally effective amount of the astaxanthin as an additive in a food substance or beverage. The food substance can include items processed for human consumption as well as pet or other animal foods. The incorporated nutritionally effective amount can be an amount that is sufficient to be physiologically active.

Another aspect of the invention is a diluted, purified *Adonis palaestina* carotenoid composition comprising astaxanthin di-ester dissolved or dispersed in a diluent such as a cosmetically acceptable diluent. Such a composition can be prepared using the previously described concentrate. In some embodiments, the composition includes at least one additional carotenoid in free or esterified form. A use of this aspect of the invention includes a light-protective amount of the astaxanthin contained in a cream, lotion, or ointment adapted for topical application to human skin. The amount of astaxanthin present in such a composition is typically about 1 to about 100 mg per day.

The present invention has several benefits and advantages.

One benefit of the invention is that large quantities of astaxanthin can now be economically produced in purified concentrated products for use in supplement formulations.

A advantage of the invention is that the use of the improved *Adonis palaestina* plants disclosed herein that have astaxanthin-rich petals as source material makes the production of astaxanthin commercially viable and efficient.

Another benefit is that *Adonis palaestina* provides a host that is economically advantageous because of the xanthophyll composition and concentration of astaxanthin in the petals.

In addition to the exemplary aspects and embodiments described above, further aspects and embodiments will become apparent by study of the following descriptions.

DEFINITIONS

In the disclosure that follows, a number of terms are used. In order to provide a clear and consistent understanding of the specification and claims, including the scope to be given such terms, the following definitions are provided:

Astaxanthin. "Astaxanthin" means a red carotenoid pigment, specifically, 3,3'-dihydroxy-β,β-carotene-4,4'-dione. Astaxanthin can be present in an *Adonis* oleoresin in combination with other ketocarotenoids including but not limited to echinenone, 3-hydroxyechinenone, adonirubuin, 3'-hydroxyechinenone, and adonixanthin. Astaxanthin is typically present as a mixture of mono- or di-$C_8$-$C_{20}$ fatty acid esters, along with small amounts of free astaxanthin, e.g. 1 to about 10 weight percent of the free and esterified carotenoids. Illustrative plant fatty acids contain 8 to about 20 carbon atoms in a straight chain with zero to about three ethylenic unsaturations per molecule. More usually, the fatty acid present in an astaxanthin ester is a $C_{12}$-$C_{18}$ fatty acid that contains zero to three ethylenic unsaturations in each chain. Such illustrative fatty acids include lauric, myristic, palmitic, palmitoleic, stearic, oleic, linoleic, linolenic, pentadecanoic, capric, and acids.

Astaxanthin content. "Astaxanthin content" means grams (g) of astaxanthin per kilogram (kg) of plant tissue dry weight measured using the absorbance of a hexane solution measured at 467 nm and an extinction coefficient of 2100. Astaxanthin content includes free astaxanthin and various esterified astaxanthin species reported as free astaxanthin.

Carotenoids. "Carotenoids" means a class of yellow to red, fat-soluble pigments.

Cardenolides. "Cardenolides" means toxic glycosylated steroids.

Cardenolide content. "Cardenolide content" means milligrams (mg) cardenolide per kilogram (kg) of plant tissue dry weight measured as cymarin equivalents.

Desglucocheirotoxin. "Desglucocheirotoxin" is a cardenolide.

Extraction. "Extraction" means obtaining of one or more chemicals from plant tissue.

Light protection effective amount. "Light protection effective amount" means at least an amount that provides photoprotection to ultraviolet light when admixed with another, photosensitive composition.

Oleoresin. "Oleoresin" means carotenoids and other materials extracted from an *Adonis palaestina* plant.

Peonidin. "Peonidin" means a bluish-red water-soluble anthocyanidin, normally present in the blotch at the base of each *Adonis* petal (the "eye" at the base of the flower) and used in the food industry to color acidic foods.

Petals. "Petals" means the individual segments or members of the corolla of a flower, usually colored or white.

DETAILED DESCRIPTION OF THE INVENTION

It is intended that the embodiments disclosed herein are to be considered illustrative rather than limiting.

The present invention provides newly developed plants of *Adonis palaestina* and the regenerable portions thereof. The flower petals and flower heads of these plants contain astaxanthin that can be extracted. The flower petals and flower heads of these plants include a relatively enhanced amount of astaxanthin and a reduced amount cardenolides than are present in standard (wild) *Adonis palaestina* plants. The petals contain similar astaxanthin isomer profiles to those in *H. pluvialis*. Farmed salmon pigmented by *Adonis* astaxanthin produced similar astaxanthin profiles to those obtained from wild salmon. A combination of optimised agronomy and conventional breeding work has developed petals-only preparations containing 3.8% astaxanthin per unit dry weight.

The *Adonis* astaxanthin, although exhibiting lower bioavailability (16-21% lower) than synthetic astaxanthin, produced comparable levels of fillet pigmentation that were acceptable to consumers. The *Adonis*-produced material proved as stable, and, in the case of freezing, more stable than pigmentation achieved using synthetic astaxanthin. Overall, the material performed well in feeding and post-processing trials. The lower bioavailability (associated with the esterified nature of the *Adonis* astaxanthin compared to the free astaxanthin in the synthetic form) compared to the natural astaxanthin can be offset by the greater stability (e.g. in feed pellet production) of the *Adonis* product.

Illustratively, new lines of *A. palaestina* have been developed that have larger flowers (a diameter greater than 1.5 cm) than wild *A. palaestina*, with the following three lines being illustrative. Plants of illustrative Line PF 31 have an average flower diameter of greater than about 5 cm and an "eye" diameter of greater than 2 cm. Plants of illustrative Line PF 52 have an average flower diameter of greater than about 5 cm and an "eye" diameter of greater than 1.5 cm. Plants of illustrative Line PF 67 have an average flower diameter of greater than about 5 cm and have upright stems. Plants of this strain typically have an average flower diameter of about 4 cm to about 8 cm, about 8 to about 12 petals per flower, and an average astaxanthin concentration of about 0.4 to about 0.6 mg per flower head. Thus, a preferred flower head has a diameter of about 5 to about 8 cm, and more usually about 5 to about 6 cm. The "eye" diameter is typically about 1.4 cm, and is often greater than about 1.5 cm.

The astaxanthin content in the dry flowers of a plant of the present invention is at least about 0.4 mg per flower, and is typically about 0.4 to about 0.8 mg per flower as discussed further below, compared to about 0.15 to about 0.25 mg per flower for the previously-discussed, patented *A. aestivalis* 'Loders Red'. Preferably, the amount is about 0.5 mg to about 0.8 mg, and more preferably the amount is about 0.6 mg to about 0.8 mg per flower. The astaxanthin concentration of the flowers of the present invention is about 14 to about 20 g astaxanthin per kg flower dry weight compared to about 6 to about 9 g/kg for 'Loders Red'. The plants also flowered earlier in Ireland in the summers of 2002-2005 than did *A. aestivalis* 'Loders Red', offering potential for earlier harvest.

The extracted carotenoids of a contemplated flower contain about 75 to about 90 weight percent astaxanthin mono-ester, di-ester and free astaxanthin, along with about 5 to about 10 weight percent lutein, about 2.5 to about 5 weight percent adonixanthin and less than about 1 percent of adonirubin, β-carotene, 3-hydroxyechinenone and 4-hydroxyechinenone. More typical amounts are about 80 to about 85 weight percent astaxanthin diester, about 5 to about 7 weight percent each of free astaxanthin and lutein, about 2.5 to about 5 weight percent adonixanthin, and less than about 1 percent of each of adonirubin, β-carotene, 3-hydroxyechinenone and 4-hydroxyechinenone.

The contemplated *Adonis palaestina* flower petals are substantially free of canthaxanthin (β,β-carotene-4,4'-dione) so that a contemplated extract prepared from the flower petals is also free of canthaxanthin. Canthaxanthin is present in *Phaffia rhodozyma* and *Haematococcus pluvialis*, and is also typically present in extracts prepared from those organisms.

The invention includes the cultivation of such plants for the purpose of obtaining astaxanthin, the extraction of astaxanthin, and the astaxanthin so obtained and a higher astaxanthin concentration so obtained.

Seeds from crossing the parental strain of *Adonis palaestina* that was obtained from the Golan Heights region in Israel and from which the preferred cultivars were obtained by simple self-crossings to maximize desired traits were deposited under the designation 'PF POP' with National Collections of Industrial, Food and Marine Bacteria (NCIMB), 23 St Machar Drive, Aberdeen, Scotland, AB24 3RY, United Kingdom. Those seeds were received on 25 May 2005 and were accepted for patent purposes on 31 Aug. 2005 under the Budapest Treaty. Access to this deposit will be available during the pendency of this application to persons determined by the Commissioner of Patent and Trademarks to be entitled thereto under 37 CRF 1.14 and 35 USC 122. Upon allowance of any claims in this application, all restrictions on the availability to the public of these varieties will be irrevocably removed. *Adonis palaestina* plants of this invention can be prepared using plants that mature from seeds of this deposited strain.

The present invention also contemplates the pollen and an ovule of a contemplated plant. The regenerable portion of a contemplated plant is also itself contemplated and includes cells selected from the group consisting of embryos, meristems, pollen, leaves, anthers, roots, root tips, and flowers, or protoplasts or callus derived therefrom. Methods for regenerating plants from cells are well known to those skilled in the art, and dicotyledonous plants such as marigolds are particularly amenable to such regeneration.

Plants of this invention such as those prepared from seeds of plants of the deposited strain typically have an average flower diameter (size) of about 5 to about 7 cm, about 8 to about 12 petals per flower, and an average astaxanthin concentration of about 0.4 to about 0.8 mg per flower head. These plants produce flowers that contain about 0.193 weight percent 95% ethanol-extractable cardenolides based on dry flower weight (about 10 to about 15% water), and more preferred plants provide flowers whose petals contain about 0.1 weight percent or less. The flowers of standard *Adonis palaestina* plants typically contain about 0.36 percent by dry flower weight cardenolides that are extractable by 95% ethanol and quantified as cymarin equivalents.

An oleoresin prepared from a contemplated *Adonis palaestina* comprised of free or fatty acid esters of astaxanthin is also contemplated. As is well known in the art, an oleoresin is a solid extract of plant tissues that contains plant pigments such as astaxanthin in free and esterified forms, sometimes accompanied by small amounts of other plant products and pigments such as other xanthophyll esters, free xanthophylls and other carotenoid pigments, as well as small amounts of the extracting solvent such as hexane or acetone.

In an illustrative oleoresin preparation, astaxanthin esters and other free and esterified xanthophylls and carotenes, are extracted from dried *Adonis palaestina* flowers with an organic solvent having a boiling point at one atmosphere of about 110° C. or less, such as hexane, acetone, ethyl acetate or the like. It is preferred that the extracting solvent be immiscible with water, so that solvents such as the hydrocarbons hexane, 2,3- and 2,4-dimethyl-pentane, 2- and 3-methylhexane, heptane, cyclohexane, 1-, 2- and 3-hexenes, the 1-, 2- and 3-heptenes, and cis and trans isomers of each, and the like are preferred. Use of a hydrocarbon extractant solvent helps to minimize the amount of cardenolides that are extracted. The extraction is carried out according to procedures known in the art for extraction of plant materials with organic solvents. Extraction can also be carried out with an extractant that is gaseous at one atmosphere and ambient room temperature. One such extraction is taught in U.S. Pat. No. 5,512,285 in which tetrafluoroethane, and particularly 1,1,1,2-tetrafluoroethane (boiling point −26° C.), in liquid form is disclosed as the extracting solvent. Super-critical carbon dioxide ($CO_2$) is a well-known extractant that is also useful herein as is illustrated hereinafter.

The solvent(s) is removed, resulting in an extract that contains a high level of the astaxanthin esters as well as free xanthophylls and xanthophyll esters, and is about 99 percent and preferably about 99.9 percent free of the extracting organic solvent; i.e., contains less than about 1 percent and preferably less than about 0.1 percent organic solvent by weight. The resulting solvent-free extract is referred to as an *Adonis* oleoresin or more preferably as an astaxanthin-containing *Adonis* oleoresin. The oleoresin contains the same carotenoids in substantially the same relative amounts as are noted above to be present in the contemplated flower petals. An astaxanthin-containing *Adonis* oleoresin contains substantially less cardenolides than are present in the flower petals, with cardenolides constituting less that about 0.01 weight percent of the oleoresin.

A carotenoid composition, free of canthaxanthin, that comprises purified astaxanthin; i.e., astaxanthin-containing *Adonis* oleoresin, dissolved or dispersed in a diluent is also contemplated. A contemplated diluent can be a solid such as a wax or hydrocarbon that is solid at about 40° C., a liquid or a gel at ambient temperatures. Illustrative liquids and gels include cosmetic vehicles that are well known in the cosmetic arts, and include oil-in-water and water-in-oil emulsions, as well as natural oils and synthetic oils such as the silicone oils.

One embodiment of a purified concentrate is a solid to semi-solid that includes the mixed esters of astaxanthin of an *Adonis* oleoresin present at about 2 to about 10 percent by weight, and preferably at about 5 percent by weight. In some preferred embodiments, the concentrate includes at least one additional carotenoid in free or esterified form in a different concentration from that found in *Adonis* oleoresin. Thus, some embodiments contain a carotenoid not present in the oleoresin, whereas other embodiments contain a carotenoid present in the oleoresin, but in an amount that is enhanced by at least 10 percent and preferably by at least 20 percent over that present in the oleoresin. The added carotenoid can be present in an amount that is several times that found in the oleoresin.

A contemplated food supplement comprises a reduced cardenolide, astaxanthin-containing *Adonis* oleoresin dissolved or dispersed in a comestible diluent medium. This food supplement can thus be prepared by suitable purification of a before-described oleoresin as by dissolution, filtration and removal of cardenolides, followed by dissolution or dispersion of the purified carotenoids in an appropriate comestible diluent medium such as an edible vegetable oil. A contemplated food supplement is prepared from an astaxanthin-containing *Adonis* oleoresin (concentrate) having a reduced amount of cardenolide; i.e., contains less that about 0.01 weight percent cardenolides.

One carotenoid composition as discussed above comprises a nutritionally effective amount of astaxanthin-containing *Adonis* oleoresin dissolved or dispersed in a comestible diluent medium that is present in unit dosage form suitable for oral administration such as packets, tablets, capsules, and powders in vials or ampoules. Such a nutritionally effective amount is an amount that is sufficient to be physiologically active and is typically about 4 to about 500 mg.

Another aspect of the invention is a diluted, purified *Adonis palaestina* carotenoid composition comprising astaxanthin-containing *Adonis* oleoresin dissolved or dispersed in a diluent such as a cosmetically acceptable diluent. Such a composition can be prepared using the previously described concentrate. In some embodiments, the composition includes at least one additional carotenoid in free or esterified form. One contemplated composition includes a light-protective amount of astaxanthin contained in a cream, lotion, or ointment adapted for topical application to human skin. The amount of astaxanthin present in such a composition is typically about 1 to about 100 mg per day, and preferably about 2 to about 10 mg per day.

In some embodiments, the comestible diluent medium is an edible triglyceride oil. The 4-keto-β-ionene ring-containing carotenoid (e.g., free astaxanthin or astaxanthin ester or both) content of the food supplement admixture is typically about 0.2 to about 40 percent by weight, and more preferably about 2 to about 20 weight percent. Exemplary edible oils include candelilia, coconut, cod liver, cotton seed, menhaden, olive, palm, corn, soybean, peanut, poppy seed, safflower and sunflower oil. The use of oil having a relatively high concentration of unsaturated fatty acids is preferred; i.e., the use of oil having an iodine value of about 100 to about 150 is preferred. The admixture is typically carried out using a high shear mixing apparatus, as is well known. Co-solvents and additives such as ethanol and α-tocopherol, respectively, can also be present as is noted in U.S. Pat. No. 5,382,714.

The astaxanthin-containing composition can also be provided in the form of generally spherical small pellets conventionally referred to as "beadlets" that contain 0.5 to about 20 weight percent, and preferably about 1 to about 4 percent, of free astaxanthin esterified astaxanthin and one or more carotenoids such ass are present in an *Adonis* oleoresin. These beadlets can be used admixed in a desired amount into human food such as ready to eat cereals as is disclosed in U.S. Pat. No. 5,270,063 or admixed into chicken or other animal feed as are the beadlets or other particles disclosed for the feed additive in U.S. Pat. No. 5,849,345, No. 5,695,794, No. 5,605,699 and No. 5,043,170.

Exemplary beadlets are water-insoluble and are prepared by encapsulation of an astaxanthin-containing composition by cross-linked gelatin or an alginate such as sodium alginate as is disclosed in U.S. Pat. No. 4,670,247. In accordance with that patent, a water-insoluble beadlet containing the desired carotenoid(s) is prepared by forming an emulsion containing the carotenoid(s), water, gelatin, and a sugar. The emulsion is converted into droplets that are individually collected in an excess mass of starchy powder in such a manner that the particles from the droplets are kept separated from each other until their particulate form is permanently established. The astaxanthin-containing particles are separated from the excess starchy collecting powder, and heat-treated at a temperature of about 90° C. to about 180° C. The heat treatment step insolubilizes the gelatin matrix of the beadlet by a reaction between the carbonyl group of the sugar with the free amino moieties of the gelatin molecule. The resulting beadlets are water-insoluble and exhibit increased stability to the stresses of feed pelleting. The cross-linking process utilizes the ingredients employed in making the beadlet and does not require addition of a cross-linking reagent or additive to the composition.

U.S. Pat. No. 5,695,794 discloses another form of beadlets that can be adapted for use herein as an additive for animal feed. Thus, beadlets having diameters of about 30 to about 55 microns are prepared by spraying a molten solution of a desired amount of astaxanthin in a hydrogenated vegetable oil such as hydrogenated cotton seed oil, wheat-germ oil, safflower oil, soybean oil and the like, that also can contain mono- and diglycerides such as those prepared from hydrogenated soybean mono- and diglycerides, cottonseed mono- and diglycerides and the like, as well as citric acid and 2,6-di-tert-butyl-4-methylphenol (BHT) as antioxidants. Other antioxidants such as ethoxiquin, vitamin E and the like can also be used, as is well known. The molten mixture is sprayed at a temperature of about 160° F. (about 70° C.) into a cyclonic air stream of a spray chiller such as available from Niro, Inc., Columbia, Md. to produce the beadlets that solidify on cooling. The cooled beadlets are dusted with an anticaking agent such as fumed silica, calcium phosphate, powdered starch or cellulose as are well known to form the beadlets that are preferably added to the feed as supplement. An exemplary beadlet contains about 10 to about 100 milligrams of astaxanthin per gram (mg/g) and preferably at about 10 to about 50 mg/g.

Animal feeds to which a contemplated astaxanthin-containing carotenoid composition is added are well known in the art. The above-noted U.S. Pat. No. 5,849,345, No. 5,695,794, No. 5,605,699 and No. 5,043,170 provide exemplary diets that are particularly useful for poultry. U.S. Pat. No. 5,935,624 and No. 2,918,370 provide further illustrative poultry diets U.S. Pat. No. 5,258,189 teaches the addition of beta-carotene to a ready to eat cereal product for humans in which the beta-carotene is admixed with a cooked cereal product dispersed in a vegetable oil or in dry form. An astaxanthin carotenoid composition can be used at a desired level in place of beta-carotene in a similar food product.

Another composition suitable for use as a food supplement comprises an astaxanthin composition dissolved or dispersed in a comestible medium. This composition contains astaxanthin-containing xanthophylls that are free alcohol (or keto) compounds as compared to the esters that are present in an *Adonis* oleoresin.

Methods are well known for saponifiying oleoresins to provide free xanthophylls. See, for example, Tcyczkowski et al., *Poultry Sci.*, 70(3):651-654, 1991; and U.S. Pat. No. 5,382,714 that crystallized lutein from the saponified marigold oleoresin by the addition of organic solvents.

In addition, Ausich et al. U.S. Pat. No. 5,648,564 teaches the production of crystalline lutein from an oleoresin by admixing the oleoresin with a composition containing propylene glycol and an aqueous alkali, preferably potassium hydroxide, to form a reaction mixture of which oleoresin and propylene glycol together constitute at least 75 weight percent. The reaction mixture so formed is maintained at a temperature of about 65° C. to about 80° C. for a time period (typically at least 3 hours) sufficient to saponify the xanthophyll ester and form a saponified reaction mixture that contains free xanthophyll in the form of crystals. The saponified extract is admixed with a diluting amount of water to dissolve the water-soluble impurities and reduce the viscosity of the reaction mixture. The diluted admixture is gently admixed until homogeneous and then filtered to collect the xanthophyll crystals. The collected xanthophyll crystals are washed with warm water, and dried. No organic solvent other than propylene glycol is used in the isolation and purification of the xanthophyll from the xanthophyll ester-containing oleoresin. The dried xanthophyll crystals so formed are typically admixed with a comestible medium such as the triglyceride discussed elsewhere. The xanthophyll content of the admixture is typically about 0.1 to about 35 percent by weight, and preferably about 1 to about 10 percent by weight.

Methods are well known for saponifiying astaxanthin esters to provide the free xanthophyll. See, for example, Kamata et al., *Comp. Biochem. Physiol.*, 86B(3):587-591, 1987; and Yuan et al., *J. Agric. Food Chem.*, 47:31-35, 1999, that both saponify astaxanthin esters under nitrogen.

For fatty acid analysis, Kamata et al. saponified a purified astaxanthin diester from *Adonis aestivalis* using 0.1 N methanolic KOH and heating at 100° C. for 40 minutes under nitrogen. After saponification, 0.5N HCl was added to acidify the sample and astacene, a structural transformant of astaxanthin, was extracted with petroleum ether.

Yuan et al., above, identified a saponification method for the hydrolysis of astaxanthin esters in pigment extract of *Haematococcus pluvialis* without significant degradation or structural transformation of astaxanthin. Complete hydrolysis of astaxanthin esters was achieved in six hours for different concentrations (10-100 mg/l) of pigment extracts using 0.018 M methanolic NaOH under nitrogen in darkness. With a higher concentration of methanolic NaOH solution, the reaction rate of hydrolysis was high, but astaxanthin degradation occurred significantly.

In another embodiment, flowers of a plant of the present invention are extracted with a hydrophilic solvent such as 95% ethanol to remove cardenolides, and dried to provide flower petals that can be fed to animals as is or after comminution. The extract so prepared can be a source of cardenolides for medicinal uses.

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLES

The following examples are provided to further illustrate the present invention and are not intended to limit the invention beyond the limitations set forth in the appended claims.

Example 1

Method to Obtain Low-Cardenolide, High Astaxanthin Oleoresin

Research was conducted to develop methods of obtaining astaxanthin that would increase the quality of the astaxanthin oleoresin in terms of increased astaxanthin quantity, reduced quantity of non-astaxanthin carotenoids and reduced cardenolide quantity.

Astaxanthin yields in excess of 5 kg astaxanthin per hectare have been achieved from *A. aestivalis* 'Loders Red' by hand harvesting of flowers in field trials around Europe and New Zealand, with astaxanthin contents of 10-20 g astaxanthin per kg dried flowers. Mechanical harvesting of flowers (using a modified grass harvester) and generation of a petal-only preparation (using a de-bearder plus air separation) has been achieved. The petal preparation (that can be generated from either hand- or mechanically-harvested flowers) resulted in an increase in astaxanthin content from 9.3 to 23.0 g astaxanthin per kg dried tissue for *Adonis aestivalis* 'Loders Red' and from 16.3 to 38.7 g/kg for *Adonis palaestina* strain PF52, which are higher than any other natural source of astaxanthin (*Haematococcus* approximately 1.5 g/kg; *Phaffia* approximately 0.5 g/kg).

Furthermore, the absence of green tissue reduced the volume of solvents needed for extraction and reduced the level of total non-astaxanthin carotenoids such as beta-carotene in the extract. Oleoresin extracted from whole flowers of *Adonis aestivalis* 'Loders Red' or *Adonis palaestina* PF52 contained about 8.9 to about 13.6% non-astaxanthin carotenoids. HPLC analysis of the hand-harvested whole flower preparation showed a maximum of 1.3% non-astaxanthin carotenoids (primarily lutein) and a reduction in chlorophyll content by 84%.

Oleoresin rich in astaxanthin can be produced by grinding flowers or petals and by adding hexane and stirring for a time sufficient to extract the hexane-soluble carotenoids (e.g., about an hour), followed by vacuum filtration and hexane removal. The use of hexane alone as compared to hexane and ethanol as used in U.S. Pat. No. 5,453,565 results in an 82% reduction in total cardenolide content in the dried pigment mixture, which can be increased to a 97% reduction by optimizing the period and conditions of extraction to maximize the isolation of astaxanthin (hexane-soluble) and minimize the isolation of cardenolides (largely hexane-insoluble, apart from non-glycosylated cymarin). The dried pigment mixture obtained can be taken up by dissolving in an organic solvent or oil, such as fish oil or vegetable oil. Astaxanthin preparations with reduced cardenolides can be provided in the fish growth cycle without increasing mortality.

Example 2

Genetic Improvement of *A. palaestina*

Seed of a large-flowered *A. palaestina* was collected from the Golan Heights of Israel. The seed was planted, resulting larger flowers were crossed and new seed collected. The new seed was planted and flowers were again selected for flower size, while maintaining the intense red color of the flowers. Selected lines within the large-flowered population have produced flowers up to 3 times the diameter of standard *Adonis palaestina* flower (Table 1, below), exhibiting useful variation in petal length, width, number and astaxanthin content, as well as peonidin content (the anthocyanin generally present in the dark central "eye" of each flower).

TABLE 1

Flower characteristics of selected individual plants of *A. palaestina*

| Line | Flower diameter (cm) | Petal Number | Astaxanthin Conc. (mg/flower) | Astaxanthin Conc. (g/kg dry petals) | Peonidin Conc. (g/kg flowers) |
|---|---|---|---|---|---|
| Standard *A. palaestina* | 1.9 | 21 | 0.209 | 7.9 | 30.8 |
| DP 003 | 4.9 | 8 | 0.466 | 19.1 | 15.9 |
| DP 005 | 6.7 | 8 | 0.581 | 22.7 | 33.9 |
| DP 006 | 2.8 | 41 | 0.550 | 24.6 | 27.9 |
| DP 008 | 3.7 | 20 | 0.500 | 20.7 | 25.4 |
| DP 009 | 5.7 | 8 | 0.489 | 22.4 | 12.9 |
| DP 010 | 5.3 | 8 | 0.467 | 19.7 | 26.9 |
| DP 011 | 6.2 | 9 | 0.565 | 24.8 | 27.3 |

Table 2, below, shows the minimum, maximum and mean values for several traits of the large-flowered *A. palaestina* contemplated herein.

TABLE 2

| Trait | Minimum | Maximum | Mean |
|---|---|---|---|
| Flower diameter (cm) | 0.8 | 7.0 | 4.0 |
| Eye diameter (cm) | 0.0 | 5.0 | 1.4 |
| Petal number | 7 | 15 | 8 |
| Astaxanthin content (g/kg) | 8.1 | 22.1 | 17.6 |
| Bud number per plant | 4 | 117 | 30 |

Selected *A. palaestina* plants were hybridized with standard *Adonis aestivalis* to develop increased petal number and ease of germination into the large-flowered plants. These plants were not fertile and could not be used to provide further seed.

Example 3

Novel Products from *Adonis palaestina*

The differences in reported physiological activity between the perennial (highly active) and annual *Adonis* species (less active) can be attributed to both quantitative and qualitative differences in cardenolide content. The average total cardenolide content of dried *A. vernalis* tissue is approximately 0.5% (weight per weight), compared to 0.08% (*A. palaestina*), 0.1% (*A. aestivalis*) and 0.2% (*A. aleppica*) among the annual species. *A. vernalis* contains approximately 30 different cardenolides, compared to 8 (*A. aestivalis*), 9 (*A. palaestina*) and 10 (*A. aleppica*). Furthermore, several of the *A. vernalis* cardenolides missing from the annual species include major cardenolides such as adonitoxin (the major *A. vernalis* cardenolide, consisting of 15-20% of the total cardenolide content) and desglucocheirotoxin.

Following flower harvest of *A. palaestina* (manual or mechanical), a conservative estimate of 2 tons/hectare of plant dry matter remain in the field in the form of stems, stalks and leaves. This amount of biomass should contain approximately 0.08% cardenolides; *A. vernalis* is usually harvested around flowering to maximize cardenolide yield. Harvesting can be achieved mechanically using a standard mower type harvester or (by hand) using sickles or scythes. The fresh tissue should be dried rapidly to prevent quality deterioration, e.g. on a flat bed drier. The dried material can be sold in this form, or cut into smaller-sized preparations or powdered by mechanical grinding or milling, or extracted to produce the herb fluid extract, oleoresin or tinctures.

After extraction of the dried flowers in hexane (to isolate the astaxanthin), followed by drying to eliminate hexane residues, the flower powder is extracted with ethanol to yield a tincture containing approximately 98% of the original cardenolide content of the flowers (the remainder extracting into the hexane). This procedure provides approximately 25% of the tincture yield of cardenolides that extraction of the dried green material (stems, stalks and leaves) achieves (estimated above), but without additional harvesting, drying and processing costs, except for drying and ethanol extraction.

Peonidin can be removed and isolated by ethanol extraction of *Adonis* flowers after hexane extraction from low-cardenolide lines.

Organic astaxanthin can be produced for organic salmon culture from low-cardenolide *Adonis palaestina* either as pulverized petals or as ethanol-extracted oleoresin.

Example 4

Carotenoid and Fatty Acid Components of an *Adonis* Oleoresin

An oleoresin prepared from a preferred *Adonis palaestina* plant was assayed for the identities of the carotenoids present and the identities of the carotenoid-esterifying fatty acids. The results of those assays are shown in Tables 3 and 4, below.

TABLE 3

Carotenoid Profile

| Carotenoid | Weight Percent |
| --- | --- |
| Astaxanthin diester | 81.1 |
| Lutein | 6.9 |
| Free astaxanthin | 6.4 |
| Adonixanthin | 3.3 |
| Adonirubin | 0.8 |
| Beta-carotene | 0.8 |
| 3-hydroxyechinenone | 0.3 |
| 4-hydroxyechinenone | 0.3 |
| Canthaxanthin | Zero |

TABLE 4

Astaxanthin Di-ester Profile*

| Fatty Acid | Weight Percent |
| --- | --- |
| C12:0 | 13.5 |
| C14:0 | 17.3 |
| C16:0 | 21.1 |
| C16:1 | 5.0 |
| C18:0 | 3.5 |
| C18:1 | 18.3 |
| C18:2 | 5.5 |
| C18:3 | 15.6 |

*Fatty acids are identified by the number of carbon atoms in the chain followed by a colon and the number of ethylenic unsaturations present in the chain.

Example 5

Stability of Astaxanthin in Fish Fed *Adonis* Oleoresin

Rainbow trout fed synthetic or *Adonis*-derived astaxanthin in a feeding trial were harvested 63 days after the feeding trial started and the astaxanthin levels were examined spectrophotometrically (Minolta Chroma Meter) and chemically (by HPLC analysis after lipid removal from the flesh extract) before and after freezing (2 months) and smoking. The initial astaxanthin levels in the feed were adjusted to achieve similar levels of pigmentation of the fish before treatments were carried out. Because pigment levels vary along the length of the fish, measurements were carried out at three positions along each fish (head, mid-body and tail). The results are shown in Table 5.

TABLE 5

Effect of freezing and smoking on astaxanthin levels in fillets of fish fed Adonis-derived astaxanthin or synthetic astaxanthin*

| Source | Treatment | Spectrophotometric (Hunter a values) Average | HPLC (mg/kg fish) Average |
| --- | --- | --- | --- |
| Adonis | Control | 6.2 | 14.5 |
|  | Smoked | 5.9 | 14.6 |
|  | Frozen | 5.6 | 13.2 |
| Synthetic | Control | 6.5 | 15.1 |
|  | Smoked | 5.8 | 14.0 |
|  | Frozen | 4.2 | 11.2 |

*Data averaged over three fillet zones.

It was clear from the different forms of assessment of flesh pigmentation that the *Adonis* oleoresin resulted in more stable pigmentation, particularly with regard to the freezing treatment where the fillets from fish fed synthetic oleoresin suffered a 26% loss in cardenolide content compared to 9% for those fed *Adonis* oleoresin (Table 5). The reason for this is under investigation. The isomeric profile of astaxanthin in the fish fed the two sources of astaxanthin were similar; it is possible that the deposition locations were different leading to greater sensitivity to loss as a result of freeze-thaw.

Example 6

Cardenolide Content in Fish Fed *Adonis* Oleoresin

Dried flower tissue contained 0.28% (w/w) cardenolides. Analysis of the six principal cardenolides detected in floral tissue revealed that they were all strophanthidin derivatives: strophanthidin (the aglycone) and the glycosides cymarin, K-strophanthin, K-strophanthoside, convallotoxin and one as-yet unidentified glycoside. Hexane extraction of the astaxanthin (the industrial standard for carotenoid isolation) largely failed to co-extract the cardenolides, resulting in a corresponding oleoresin content of 0.0016%, compared to the dried flower value.

Analysis revealed that that value was due to non-extraction of the more hydrophilic glycosides, resulting in an increase in the dominance of strophanthidin from 3.8% (ethanol extract of dried flowers) to 93.6% of the total cardenolide content in the oleoresin. The oleoresin at the level used (80 ppm astaxanthin) had no negative effect on the mortality or growth rate of the rainbow trout, whereas concentrations up to 20 times higher than that had no significant impact on the mortality of brine shrimp in these studies.

Fish that had been fed *Adonis*-derived astaxanthin in the above feeding trial were analyzed for cardenolide content; fillets from a sea bream feeding trial carried out in Japan are also available for cardenolide analysis, to extend this finding to a second, unrelated commercial fish species.

Because strophanthidin is quite highly lipophilic, cardenolide content was determined in the flesh (head, mid-fillet and tail) as well as in the skin and the intestines. A method was developed to quantify cardenolides in the fish, eliminating the lipids from the sample and maximizing the sensitivity of the assay. Analysis showed that minimal levels of cardenolides could be detected in the flesh of trout fed *Adonis* oleoresin, with slightly higher concentrations in the skin (Table 6).

TABLE 6

Levels of cardenolides in rainbow trout fed Adonis-derived astaxanthin oleoresin

| Fish tissue | Cardenolide content* |
|---|---|
| Flesh: head | 0.03 |
| Mid-section | 0.04 |
| Tail | 0.06 |
| Skin | 0.11 |
| Intestines | n/d |

*ppm cymarin equivalents;
n/d: not detectable

These results reflect the experience of medicinal use of *Adonis* cardenolides in the treatment of heart arrhythmia, in that there appears to be little or no accumulation of *Adonis* cardenolides, suggesting that the presence of trace levels of cardenolide in the astaxanthin fed to the fish does not present a health problem to consumers of fish, as the amount of cardenolide present in a standard 200 g portion of rainbow trout would contain less than 8% of the recommended safe dose of *Adonis* cardenolides when used as a herbal medicine.

Example 7

Genetic Reduction of Oleoresin Cardenolide Content

Genetic reduction of the cardenolide content of the *A. palaestina* plants by selection was investigated: a total of 235 individual plants were scored for cardenolide content, both quantitatively, using a modified Kedde's reagent (3,5-dinitrobenzoic acid in aqueous/methanolic potassium hydroxide) method, and qualitatively, using a high-resolution high-throughout HPTLC method. Analysis of the *A. palaestina* population revealed a wide range of cardenolide contents in the flowers, ranging from 0.034 to 0.464% (w/w), with an average of 0.265%. Self-pollination of these plants, followed by cardenolide analysis of the resulting progeny revealed a narrow-sense heritability value of 0.76 for cardenolide content; i.e., 76% of the variation was genetic in basis and could be improved by selection. The best 5% of the progeny populations had a mean cardenolide content of in dry petals of only 0.042%, less than 15% of the level of the parent population. Selection is on-going for ultra-low lines within these selected populations to reduce this figure even further.

High performance thin layer chromatography (HPTLC) of the petals revealed a total of 13 plant lines that exhibited the absence of one or more of the six cardenolide bands found in flower tissue. Hybridization between lines with different patterns of missing cardenolides (e.g. zero-A×zero-D can yield a double-zero recombinant, lacking both bands A and D). Seed of a total of 73 of the 78 non-reciprocal hybrids has been prepared and the progeny are under investigation, for both HPTLC profile and total cardenolide content.

An additional research area has focused on possible pleiotropic effects of reducing cardenolide content. Analysis of individual sub-populations with varying cardenolide contents revealed no significant association of cardenolide content with flower size (rP>0.05), height (r=−0.17, P>0.05), flower number (r=−0.05: p>0.05) or astaxanthin content (r=0.21; P.0.05). These data indicate that genetic lowering of cardenolide content should not confound breeding for elevated astaxanthin yield in *Adonis*. On the other hand, the cardenolides are probably anti-herbivore and possibly anti-pathogen defence chemicals within the plant, so their elimination could be hypothesised to result in reduced defence.

To test this hyopothesis, the effect of cardenolide content on the behaviour of monophagous/specialist (*Phoma adonidis*) and polyphagous/generalist pathogens (*Sclerotinia sclerotiorum*) and on a polyphagous herbivore (*Deroceras reticulatum*) was tested using (a) pure cardenolides and (b) individual *Adonis* plants differeing with respect to cardenolide content. Two different cardenolides (cymarin and strophanthidin) were assessed for their dosage effect on pathogen response. Both inhibited the growth of *Sclerotinia* but not that of *P. adonidis;* as the latter is the most important pathogen of field-grown *Adonis*, these data suggest that reducing cardenolide content should have negligible impact on disease problems. When *Deroceras* was studied, again, no association was observed between cardenolide content and slug performance or mortaility; indeed, observations revealed that slugs ate most of the petal tissue except for the base, where another pigment, an anthocyanidin, paeonidin, accumulated, indicating that this, rather than the cardenolides, was the principal defence against polyphagous pests. Again, these data suggest that the effects on crop protection needs of breeding low-cardenolide *Adonis* plants should be minimal.

Example 8

Reduction of Oleoresin Cardenolide Content by Supercritical $CO_2$ Extraction Although solvent (usually hexane) extraction of carotenoids from natural sources is the industry standard and achieves very high efficiencies, use of that solvent has several drawbacks, such as the use of high temperatures (resulting in losses as well as artefact generation) to remove most of the solvent residue plus the retention of trace residues in the oleoresin. Solvent extracted oleoresin is also unacceptable for the organic seafood market, an area at which natural sources of astaxanthin would be targeted. Supercritical $CO_2$ extraction uses lower temperatures, but also permits tailoring of the extraction conditions to maximise purification of the astaxanthin preparation. This method was used in lab-based pilot-scale trials to eliminate cardenolide content and to increase astaxanthin content by reducing the lipid content of the oleoresin.

A factorial study was carried out, varying the temperature (35-65° C.), the flow rate of the $CO_2$ (2-10 kg/hour), the operating pressure (200-400 kg/cm$^2$) and the extraction period (1-3 hours). Maximum astaxanthin concentration of the oleoresin was obtained at 45° C., 2 hour extraction period and a flow rate of 4 kg/hour; the astaxanthin content was 16.7%, compared to 10.6% from hexane extraction. This improvement resulted from reduced lipid extraction, although the astaxanthin recovery was lower (65-76%), compared to hexane extraction (84%).

Further optimization by altering the operating pressure reduced the cardenolide content of the oleoresin from 0.061 ppm (solvent) to 0.0011 ppm (300 kg/cm$^2$). Large-scale extraction systems tend to be more efficient than lab-scale systems, so scale-up of this technology could lead to further improvements.

Example 9

Gibberellic Acid and Germination

*Adonis palaestina* populations were evaluated for seed viability and germination. Although seed viability is fair (about 30 to about 70%), germination is very low. Germination has been increased to 64.7% by pre-soaking the seed in 5000 ppm gibberellic acid for 24 hours (Table 7) before sowing.

TABLE 7

Effects of pre-soaking period and temperature, and gibberellic acid (GA) concentration in pre-soak medium on % germination in *A. palaestina*

| Pre-Soak | | Gibberellic acid concentration (ppm) | | | | |
|---|---|---|---|---|---|---|
| Time (hours) | Temperature (° C.) | Zero | 1000 | 2000 | 3500 | 5000 |
| 24 | 4 | 0 | 4.3 | 10.7 | 21.4 | 28.0 |
| 24 | 16 | 0 | 8.7 | 12.6 | 25.7 | 34.7 |
| 48 | 4 | 0 | 13.7 | 20.4 | 28.7 | 40.3 |
| 48 | 16 | 0 | 22.3 | 28.7 | 45.7 | 64.7 |

A 24-hour incubation period with GA in ethanol at room temperature further improved germination; treated seed was then surface dried and could be stored for 4 weeks without significant loss of viability.

Example 10

Herbicide Effects on *Adonis palaestina*

Trials using pre-emergence herbicides showed that metribuzin(4-amino-6-tert-butyl-4,5-dihydro-3-methlythio-1,2,4-triazin-5-one) was the only broad-spectrum herbicide that could be used safely on *Adonis*. In a comparison between metribuzin and Asulox® [methyl(4-aminophenyl)sulfony-laminoformate], it was found that, although Asulox® did not affect *Adonis,* it did not achieve much weed control (Table 8).

TABLE 8

Effect of concentration of two herbicides on weed control and Adonis seedling establishment (after graminicide stress treatment)

| Herbicide | % manufacturer's recommended rate | Adonis seedling density ($m^{-2}$) | Weed density (% cover) |
|---|---|---|---|
| Metribuzin | 50 | | 56 |
| | | 1.2 | |
| | 25 | | 79 |
| | | 5.9 | |
| | 12.5 | | 85 |
| | | 12.1 | |
| Asulox ® | 100 | | 87 |
| | | 67.9 | |
| | 50 | | 74 |
| | | 85.8 | |
| | 25 | | 86 |
| | | 79.5 | |

Container trials were conducted on the effect of sand content and soil pH on metribuzin-associated *Adonis* mortality. It was clear that as sand content (but not pH) increased, so did mortality. Reducing the metribuzin level from 500 to 250 g/ha reduced plant death, while maintaining reasonable weed control; at 125 g/ha, weed control was inadequate. Furthermore, at high pH, there was a negative interaction between the organophosphate isazophos [O-(5-Chloro-1-(1-methyl-ethyl)-1H-1,2,4-triazol-3-yl) O,O-diethyl phosphorothioate] and metribuzin; again, though, the mortality induced was relatively minor (Table 9).

TABLE 9

Effect of isazophos, sand content and soil pH on Adonis seedling establishment (plants per $m^2$) following pre-emergence application of metribuzin (500 g/ha)

| pH Sand (%) | | | Soil | | |
|---|---|---|---|---|---|
| | | 6.5 | 6.8 | 7.2 | 7.5 |
| | 7.9 | 8.3 | 7.2+ | | 7.9+ |
| | isazophos | isazophos | | | |
| 84 | 75 | 77 | 67 | 65 | 77 |
| | 76 | 69 | | 59 | |
| 70 | | 78 | 80 | 78 | 75 | 86 |
| | 69 | 76 | | 63 | |
| 53 | | 80 | 87 | 82 | 89 | 83 |
| | 74 | 74 | | 69 | |
| 38 | | 86 | 79 | 86 | 87 | 80 |
| | 72 | 79 | | 76 | |

Anecdotal evidence suggests that metribuzin causes increased plant mortality in wheat and soybean crops, especially under high-pH conditions, when the seedlings are exposed to post-application stress, such as heavy rain or drought. Field trials were set up in Carrigtwohill, Co. Cork, Ireland, to test this hypothesis, although the pH value of the site was only 6.8. Seedlings emerging from metribuzin-treated soil were sprayed with a grass-specific herbicide [graminicide; (RS)-7-(4,6-dimethoxypyrimidin-2-ylthio)-3-methyl-2-benzofuran-1(3H)-one] at the seed leaf stage; this would normally be expected to "check" the seedlings (i.e.; cause a degree of non-lethal stress) when applied at the usual time (three true leaf stage). Here, 30% seedling death was observed when 500 g/ha metribuzin was used. This effect was ameliorated by using 250 g/ha metribuzin or by using 500 g/ha followed by a foliar application of urea (nitrogen can help plants to tolerate stresses) eight days after seedling emergence (Table 10). The reduced metribuzin rate resulted in increased weed growth; this could be reduced without increased seedling death by applying metribuzin (at 250 g/ha) twice, once before sowing and once after sowing (Table 10).

TABLE 10

Effect of transient stress (graminicide) on establishment of Adonis seedlings grown in the presence of pre-emergence metribuzin

| Metribuzin rate Adonis density (g/ha) | +/−Graminicide | +/−Urea (# plants $m^{-2}$) |
|---|---|---|
| 500 | | − |
| | − | 98 |
| | | + |
| | − | 65 |
| | | − |
| | + | 104 |
| | | + |
| | + | 94 |
| 250 | | − |
| | − | 103 |
| | | + |
| | − | 97 |
| | | − |
| | + | 107 |

TABLE 10-continued

Effect of transient stress (graminicide) on establishment of Adonis seedlings grown in the presence of pre-emergence metribuzin

| Metribuzin rate Adonis density (g/ha) | +/−Graminicide | +/−Urea | (# plants m$^{-2}$) |
|---|---|---|---|
| (pre) + 250 (post) | + | + | — |
|  | − | − | 100 |
|  | − | + | 105 |
|  | + | − | 102 |
| 0 | + | + | 107 |
|  | − | − | 102 |
|  | − | + | 98 |
|  | + | − | 95 |
|  | + | + | 106 |

Each of the patents, applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed is:

1. A method for the production of astaxanthin pigment that comprises cultivating plants of *Adonis palaestina* designated 'PF POP', a sample of seed having been deposited at the NCIMB, having an astaxanthin content of about 0.5 to about 0.8 mg per flower head, and extracting the astaxanthin from the petals.

2. The method of claim 1 wherein the astaxanthin content is about 0.6 mg to about 0.8 mg per flower.

3. The method according to claim 1 wherein said method comprises cultivating the plants, harvesting the flower heads or petals and extracting the astaxanthin from the harvested flower heads or petals thereof.

4. The method of claim 1 wherein the extraction of astaxanthin is conducted using hexane.

5. The method of claim 1 wherein the extraction of astaxanthin is conducted using super-critical carbon dioxide.

6. A method for the production of astaxanthin pigment that comprises cultivating plants of *Adonis palaestina* designated 'PF POP', a sample of seed having been deposited at the NCIMB, having an astaxanthin content of about 0.6 to about 0.8 mg per flower head and a flower head diameter of about 5 cm to about 8 cm, and extracting the astaxanthin from the petals using super-critical carbon dioxide.

7. The method according to claim 1 wherein said method comprises cultivating the plants, harvesting the flower heads or petals and extracting the astaxanthin from the harvested flower heads or petals thereof, wherein the extracting is conducted using super-critical carbon dioxide.

* * * * *